(12) United States Patent
Stalcup et al.

(10) Patent No.: US 6,425,923 B1
(45) Date of Patent: Jul. 30, 2002

(54) CONTOURABLE POLYMER FILLED IMPLANT

(75) Inventors: Gregory C. Stalcup, Columbia City; Antony J. Lozier, Warsaw, both of IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 09/519,690

(22) Filed: Mar. 7, 2000

(51) Int. Cl.[7] ................................................. A61F 2/36
(52) U.S. Cl. .............................. 623/23.58; 623/23.48; 606/62; 606/94
(58) Field of Search ..................... 623/23.58, 23.48, 623/23.63, 23.75; 606/62, 63, 68, 94, 192

(56) References Cited

U.S. PATENT DOCUMENTS

| | | | |
|---|---|---|---|
| 3,875,595 A | * 4/1975 | Froning | |
| 4,313,434 A | 2/1982 | Segal | 128/92 |
| 4,477,604 A | * 10/1984 | Oechsle, III | 523/116 |
| 4,662,887 A | 5/1987 | Turner et al. | 623/16 |
| 4,714,478 A | 12/1987 | Fischer | 623/23 |
| 4,772,287 A | * 9/1988 | Ray et al. | 623/17 |
| 5,102,413 A | 4/1992 | Poddar | 606/62 |
| 5,303,718 A | 4/1994 | Krajicek | 128/897 |
| 5,423,850 A | 6/1995 | Berger | 606/192 |
| 5,480,400 A | 1/1996 | Berger | 606/60 |
| 5,514,137 A | 5/1996 | Coutts | 606/62 |
| 5,549,679 A | * 8/1996 | Kuslich | 623/17 |
| 5,658,310 A | 8/1997 | Berger | 606/192 |
| 5,681,289 A | 10/1997 | Wilcox et al. | 604/175 |
| 5,827,289 A | 10/1998 | Reiley et al. | 606/86 |
| 5,951,160 A | 9/1999 | Ronk | 366/130 |
| 5,997,582 A | 12/1999 | Weiss | 623/23 |
| 6,140,452 A | * 10/2000 | Felt et al. | 528/60 |

* cited by examiner

*Primary Examiner*—Bruce Snow
(74) *Attorney, Agent, or Firm*—Jacque R. Wilson

(57) ABSTRACT

An orthopaedic implant includes a flexible bag having at least a portion thereof which is expandable under pressure; and a polymer within the bag. The orthopaedic implant is implanted within a bone by forming a cavity in the bone; inserting a flexible bag into the cavity, the flexible bag having at least a portion thereof which is expandable under pressure; pressure filling the bag with a polymer, whereby the expandable portion of the bag expands to substantially entirely fill the cavity in the bone; and hardening the polymer.

13 Claims, 5 Drawing Sheets

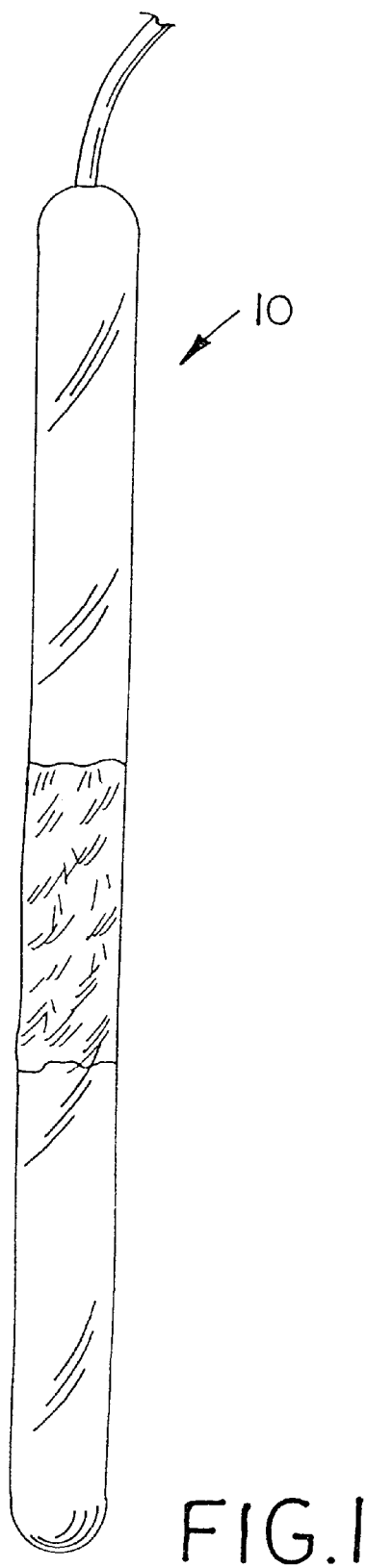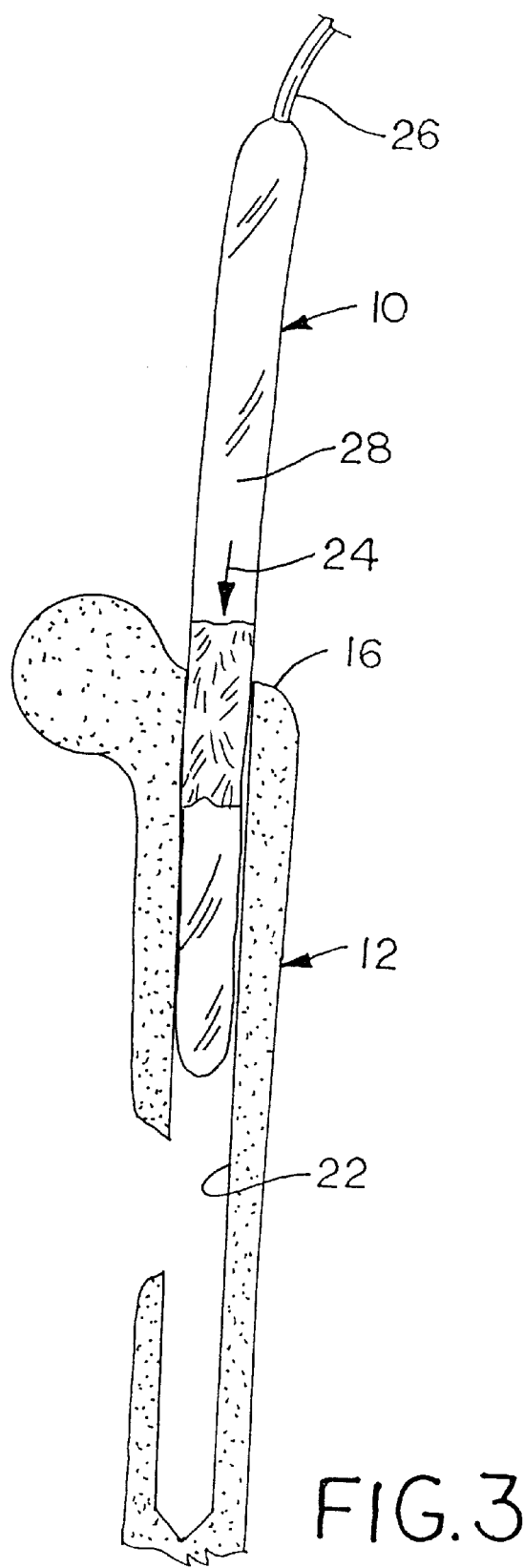

CONTOURABLE POLYMER FILLED IMPLANT

BACKGROUND OF THE INVENTION

1. Field of the Invention

The present invention relates to orthopaedic implants, and, more particularly, to implants used to fill a void in a bone.

2. Description of the Related Art

Orthopaedic implants and hardware are typically used to structurally support a bone or provide a bearing surface for articulating movement between adjacent bones. For example, a bone plate may be used to position bone fragments relative to each other and provide structural support to the bone. As a further example, a femoral hip component typically includes a femoral head providing an articulating surface with an acetabular cup implant.

It is also not uncommon for a bone to form a void therein for various reasons. For example, a void may be formed in a bone as a result of trauma, (e.g., accidents) or disease (e.g., cancer). Orthopaedic hardware such as a bone plate or intramedullary nail may span a void and provide structural support to the bone on opposite sides of the void, but typically does not fill the void.

What is needed in the art is an orthopaedic implant and method of implanting the same which allows a void in a bone to be substantially filled with minimal invasive surgery, and/or restores at least some degree of structural integrity to the bone.

SUMMARY OF THE INVENTION

The present invention provides an orthopaedic implant including a polymer filled bag which is expandable under pressure to fill a void in a bone adjacent to a cavity formed in the bone, thereby providing some degree of structural integrity to the bone.

The invention comprises, in one form thereof, an orthopaedic implant including a flexible bag having at least a portion thereof which is expandable under pressure; and a polymer within the bag.

The invention comprises, in another form thereof, a method of implanting an orthopaedic implant in a bone including the steps of forming a cavity in the bone; inserting a flexible bag into the cavity, the flexible bag having at least a portion thereof which is expandable under pressure; pressure filling the bag with a polymer, whereby the expandable portion of the bag expands to substantially entirely fill the cavity in the bone; and hardening the polymer.

An advantage of the present invention is that a void in a bone may be substantially filled with an orthopaedic implant which substantially conforms to the shape of the void.

Another advantage is that structural integrity is restored to the bone after the void is filled.

Yet another advantage is that the void in the bone may be substantially filled with the orthopaedic implant as long as a cavity providing access to the void may be formed in the bone.

Still another advantage is that the void in the bone may be substantially filled with minimal invasive surgery.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 1 is a plan view of an embodiment of an orthopaedic implant of the present invention which may be utilized in conjunction with the implanting method of the present invention;

FIG. 3 is a side, sectional view illustrating insertion of a flexible bag of the orthopaedic implant into the bone;

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 2:
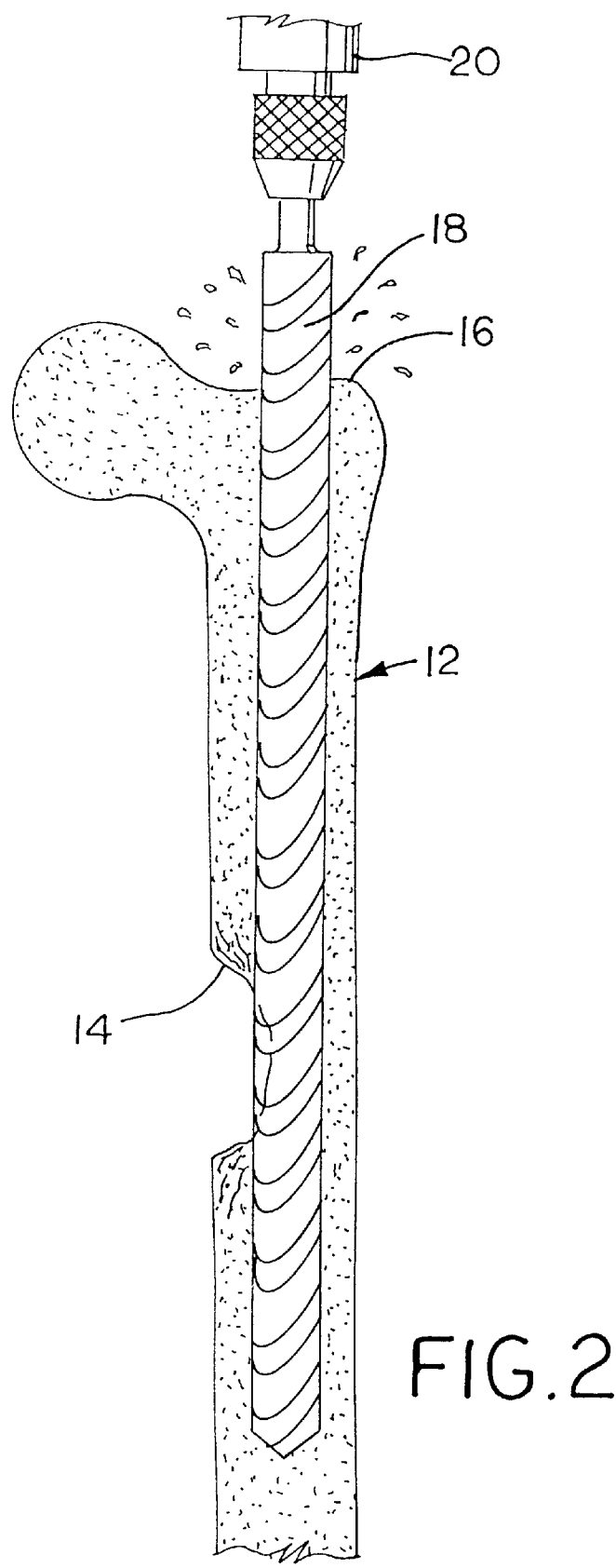
FIG. 2 is a side, sectional view illustrating the formation of a cavity in the bone relative to a void in the bone.

Referring now to the drawings, an embodiment of a method for implanting an orthopaedic implant 10 within a bone 12 will be described in further detail. Bone 12 includes a void 14 which may occur for a number of different reasons, such as disease, trauma, etc. Orthopaedic implant 10 is intended to substantially fill void 14 to provide at least some degree of structural integrity to bone 12. For example, in the event that void 14 occurred because of removal of bone by a surgeon as a result of cancer, orthopaedic implant 10 can be used to provide some degree of structural integrity to bone 12 and thereby allow mobility of the patient.

In the embodiment shown, bone 12 is in the form of a femur with a proximal end 16. A drill bit or reamer 18 (FIG. 2) driven by a drive source 20 is used to form a cavity 22 within bone 12 which extends along the intramedullary (IM) canal of bone 12. Cavity 22 extends to, and preferably past void 14 to allow proper placement and operation of orthopaedic implant 10. In the embodiment shown, cavity 22 is formed within bone 12 a distance which generally corresponds to the length of orthopaedic implant 10.

After formation of cavity 22 within bone 12 (FIG. 2), the orthopaedic implant 10 is inserted within bone 12, as indicated by arrow 24 (FIG. 3). When positioned within cavity 22, one end of orthopaedic implant 10 is closely adjacent the distal end of cavity 22, while the opposing end of orthopaedic implant 10 is closely adjacent the proximal end of cavity 22.

Figure 4:
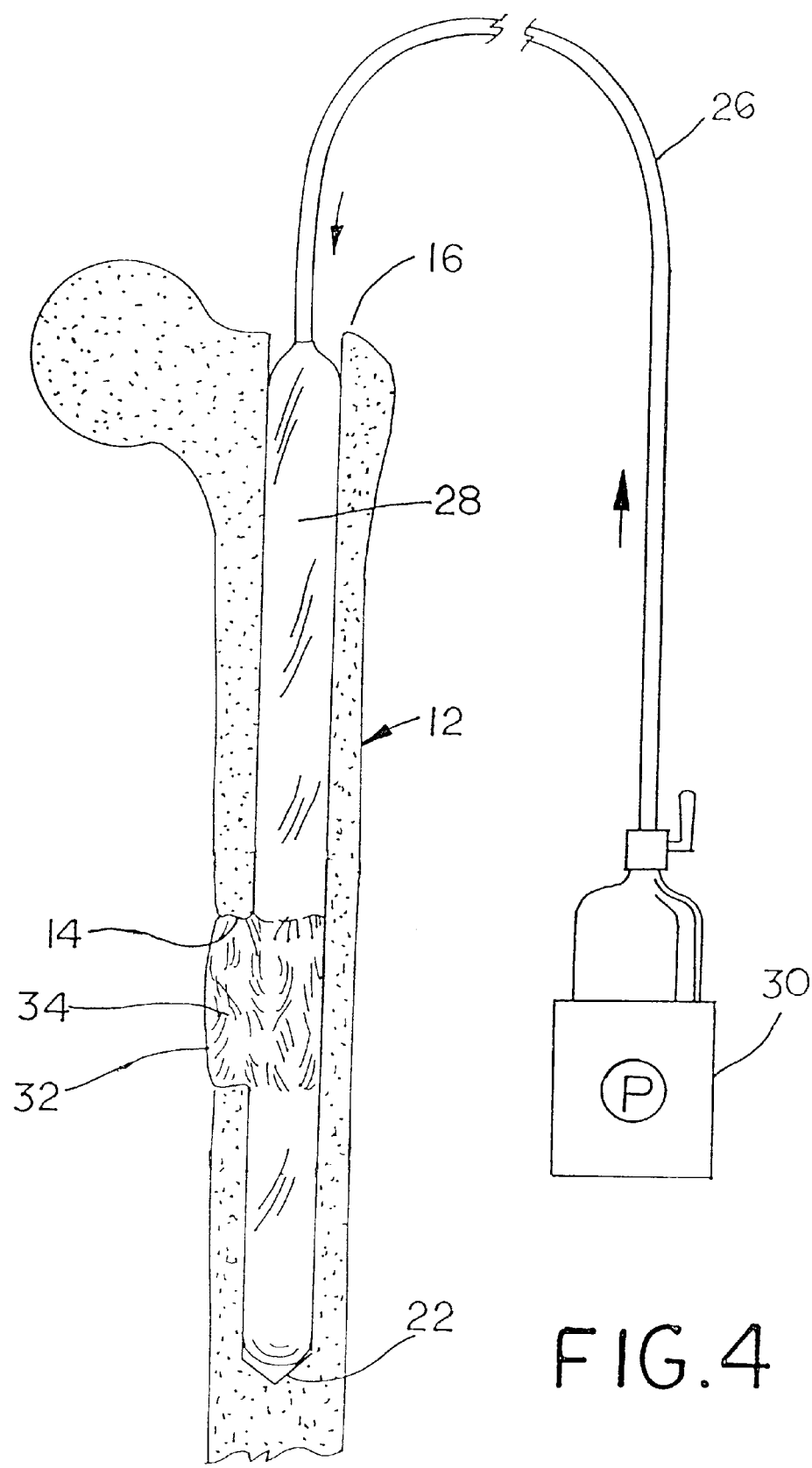
FIG. 4 is a side, sectional view illustrating pressure filling of the bag and expansion of the bag into the void of the bone.
Figure 5:
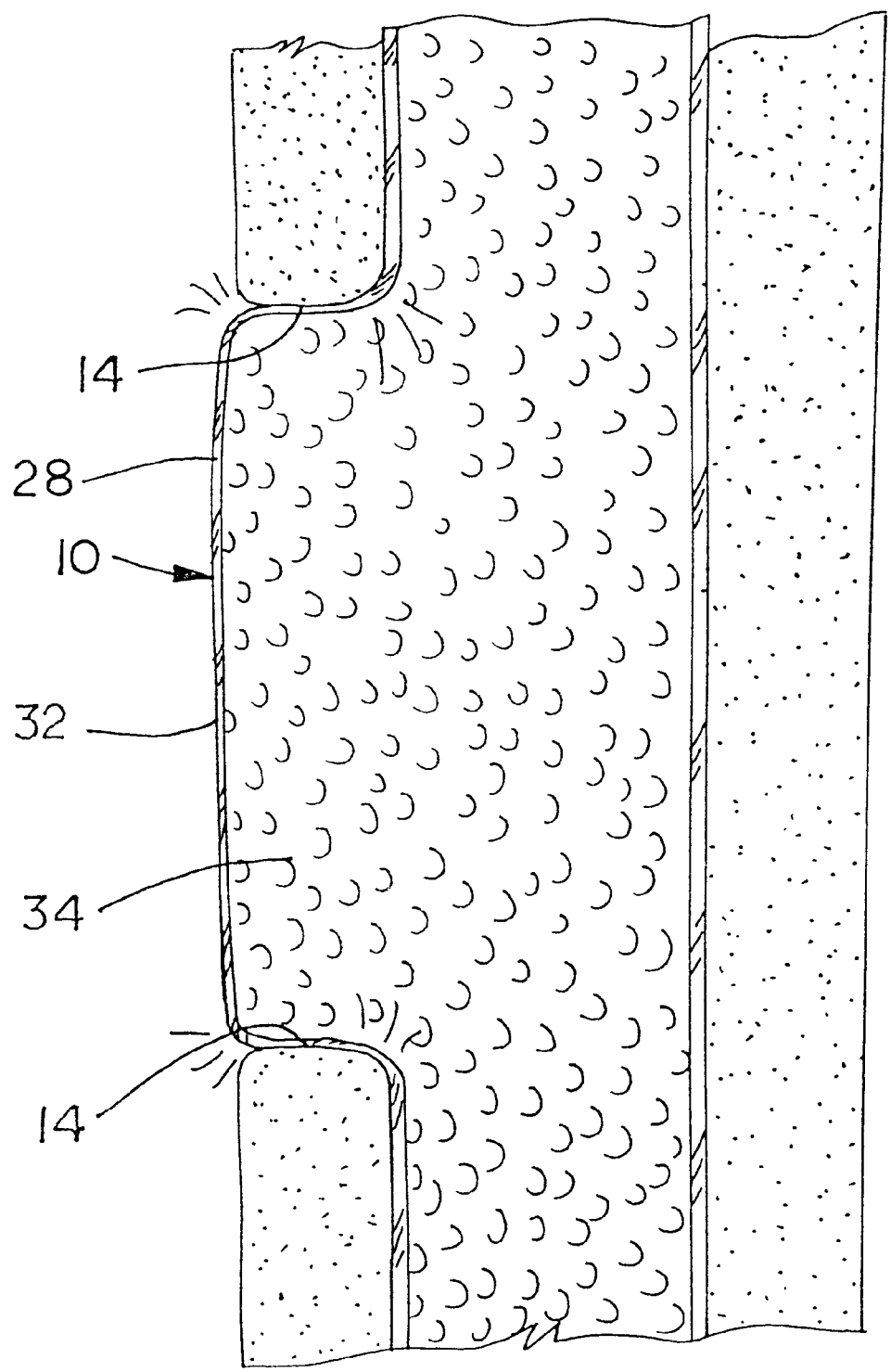
FIG. 5 is an enlarged view of the balloon portion of the bag designated at A in FIG. 4.

Orthopaedic implant 10 includes a fill hose 26 which is formed integral with or attached to a balloon or bag 28. Bag 28 is formed from an elastomeric material which is expandable under pressure. After insertion within cavity 22, bag 28 is filled with a high strength polymer which flows from a pressurized source 30 and through fill hose 26. In one exemplary embodiment, bag 28 is filled with a bioresorbable polymer. Bag 28 is pressurized to an extent causing a balloon portion 32 of bag 28 to expand into void 14 (FIG. 4). Balloon portion 32 is preferably inflated to an extent which causes bag 28 to lie generally co-planar with the outside wall of bone 12 (FIGS. 4 and 5). Polymer 34 which is pressure filled within bag 28 is then hardened to provide structural integrity of implant 10 and bone 12. Polymer 34 may be any suitable high strength polymer, and preferably is a curable polymer which hardens upon application of energy such as thermal energy, light energy, or X-ray energy or the addition of a chemical catalyst. An example of a polymer which may be utilized is polymethylmethacrylate. Bag 28 is preferably porous to allow the polymer to at least partially flow therethrough and harden within the cancellous bone surrounding bag 28.

Figure 6:
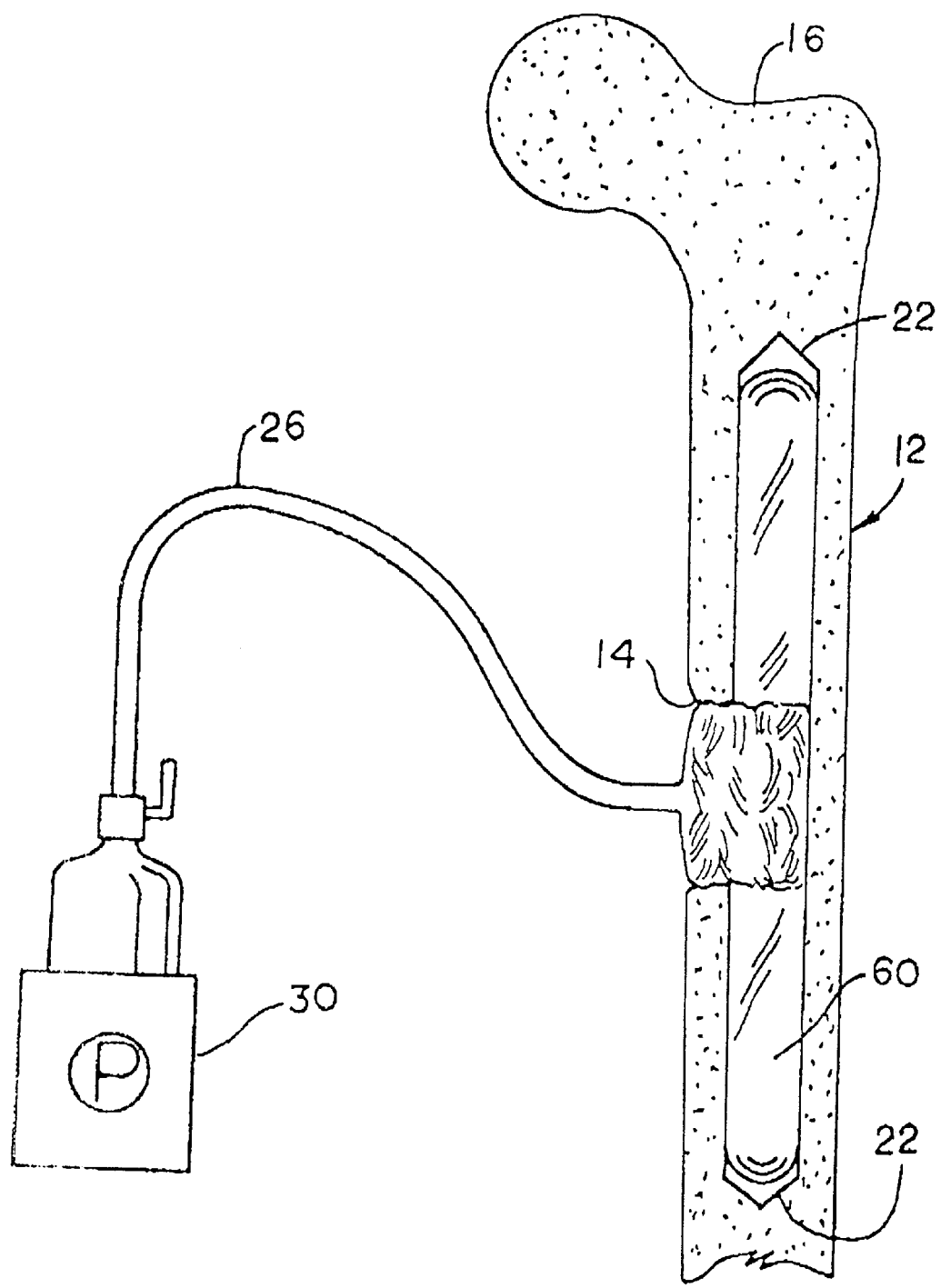
FIG. 6 is a plan view of another embodiment of an orthopaedic implant of the present invention which may be utilized in conjunction with the implanting method of the present invention.

FIG. 6 illustrates another embodiment of an orthopaedic implant 60 of the present invention which may be utilized in conjunction with the implanting method of the present invention.

Under some circumstances, it may be desirable and/or necessary to minimize the invasiveness of the surgical technique employed to insert orthopaedic implant 60 within bone 12. Accordingly, an opening may be formed through the soft tissue adjacent void 14 allowing access to void 14. Suitable instrumentation, such as flexible reamer or the like (not shown), may be used to form cavity 22 within bone 12 extending in one or both opposite longitudinal directions relative to the anatomical axis of bone 12. Orthopaedic implant is in the form of a flexible bag as described above with reference to the embodiment shown in FIGS. 1–5, and is inserted into cavity 22. A polymer compound is then injected into orthopaedic implant 60 from pressurized source 30 of polymer, thereby expanding implant 60 within and substantially filling cavity 22. The polymer within orthopaedic implant 60 is then hardened as described above.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of implanting an orthopaedic implant in a bone having a non-surgically created void, comprising the steps of:
   forming a cavity in the bone, said cavity intersecting the void;
   inserting a flexible bag into said cavity, said flexible bag having at least a portion thereof which is expandable under pressure;
   pressure filling said bag with a polymer, whereby said expandable portion of said bag expands to substantially entirely fill said cavity and said void in the bone; and
   hardening said polymer.

2. The method of claim 1, wherein the bone has a shaft and said forming step comprises forming an elongate opening generally corresponding to the intramedullary canal of the bone.

3. The method of claim 2, wherein said bag is elongate to fit in the elongate opening formed in the bone.

4. The method of claim 3, wherein the bone comprises a femur.

5. The method of claim 1, wherein the bone has a void, said cavity defined in part by said void.

6. The method of claim 5, wherein the bone has a shaft and said forming step comprises forming an elongate opening generally corresponding to the intramedullary canal of the bone, said elongate opening adjoining said void.

7. The method of claim 1, wherein said bag is comprised of an elastomeric material.

8. The method of claim 1, wherein said polymer comprises a curable polymer.

9. The method of claim 8, wherein said polymer is curable with one of thermal energy, light energy, X-ray energy and a chemical catalyst.

10. The method of claim 9, wherein said hardening step comprises hardening said polymer with a chemical catalyst.

11. The method of claim 8, wherein said polymer comprises a bioresorbable polymer.

12. The method of claim 8, wherein said polymer comprises polymethylmethacrylate.

13. The method of claim 1, wherein said bag comprises a porous bag allowing some of said polymer to pass therethrough.

\* \* \* \* \*